United States Patent [19]

Oldham et al.

[11] Patent Number: 6,074,671

[45] Date of Patent: Jun. 13, 2000

[54] METHOD OF USING LECTINS FOR CONTRACEPTION AND PROPHYLAXIS AGAINST DISEASES TRANSMITTABLE BY SEXUAL CONTACT AND CONDOM CONTAINING LECTINS

[75] Inventors: Michael J. Oldham, Ventura, Calif.; Bruce F. Rose; Howard C. Krivan, both of Carson City, Nev.

[73] Assignee: Legere Pharmaceuticals, Ltd., Carson City, Nev.

[21] Appl. No.: 09/097,669

[22] Filed: Jun. 16, 1998

Related U.S. Application Data

[63] Continuation-in-part of application No. 08/695,941, Aug. 12, 1996, abandoned, which is a continuation of application No. 08/317,599, Oct. 3, 1994, abandoned, which is a continuation-in-part of application No. 08/130,190, Oct. 1, 1993, abandoned.

[51] Int. Cl.[7] .............................. A61F 5/44; A61L 15/00; A61M 31/00
[52] U.S. Cl. .............................. 424/486; 602/77; 604/48; 604/346; 604/500; 604/514; 604/515; 604/518
[58] Field of Search ................................ 602/77; 604/48, 604/500, 514, 515, 518, 346; 424/433, 486

[56] References Cited

U.S. PATENT DOCUMENTS 4,585,615  4/1986  DeMario ................................. 376/442
5,077,198  12/1991  Shih et al. ................................. 435/7.9
5,145,859  9/1992  Fleischmann .............................. 514/356

*Primary Examiner*—Nathan M. Nutter
*Attorney, Agent, or Firm*—Vorys, Sater, Seymour and Pease

[57] ABSTRACT

In order to prevent conception and/or infection by sexually transmitted diseases (STDs) one or more lectins capable of binding sperm or agglutinable components of male ejaculate and/or the pathogenic microorganisms responsible for STDs or the carbohydrate moieties expressed on cell surfaces by which the microorganisms bind to the cells, are administered to the vagina prior to sexual intercourse. The lectins prevent conception by binding to the sperm or agglutinable components of male ejaculate to render the sperm incapable of fertilization. They also bind to the pathogenic microorganisms to render them non-pathogenic or to carbohydrates expressed on cell surfaces to prevent infection by the microorganisms or treat such infections. Lectins can also be administered to treat sexually transmitted vaginal infections. The lectins can also be applied to or contained within a condom. The condom may carry the lectins either within the hollow interior of the condom or impregnated into, linked to, or coated upon its membrane body. Lectins may also be incorporated in the same way into a surgical glove for protection against infection by pathogenic microorganisms.

15 Claims, 1 Drawing Sheet

METHOD OF USING LECTINS FOR CONTRACEPTION AND PROPHYLAXIS AGAINST DISEASES TRANSMITTABLE BY SEXUAL CONTACT AND CONDOM CONTAINING LECTINS

RELATIONSHIP TO OTHER APPLICATIONS

This application is a continuation-in-part of U.S. application Ser. No. 08/695,941, filed Aug. 12, 1996 and now abandoned, which is a continuation of U.S. application Ser. No. 08/317,599, filed Oct. 03, 1994, abandoned, which is a continuation-in-part of U.S. application Ser. No. 08/130,190, filed Oct. 01, 1993, abandoned.

BACKGROUND OF THE INVENTION

1. Field of the Invention

This invention relates generally to methods of contraception and prophylaxis against diseases transmittable by sexual contact and more particularly to a method using intravaginally administered lectins for contraception and to protect against the transmission of diseases that are transmissible by sexual contact and to treat such diseases. The invention also relates to a condom containing lectins.

2. Brief Summary of the Prior Art

Sexually transmitted diseases (STDs) are epidemic in this country and worldwide. Furthermore, other diseases that have not traditionally been considered to be STDs have also been found to be transmitted by sexual contact, e.g., hepatitis B. The medical and public health problems associated with these epidemics have motivated a search for methods of controlling these diseases by limiting their transmission from person to person. Similarly, although many methods of contraception have been employed, no universally satisfactory method has been developed.

Hitherto it has been generally agreed that barrier methods which prevent the transfer of body fluids between individuals are the most effective means of preventing transmission of such diseases. Such barrier methods are also effective contraceptive procedures. However, such methods are somewhat inconvenient and require some cooperation between individuals.

An example of a commonly used and generally effective barrier method is the use of condom by the male partner or of a similar barrier used by the female partner to provide complete isolation against transfer of bodily fluids from one partner to the other. Such devices are effective for prevention of transmission of STDs and for contraception, provided that the physical barrier remains intact. In some cases however, the condom or the like may develop microscopic leaks or may contain small and perhaps unnoticeable perforations which can permit the transfer of microorganisms or of sperm across the barrier. In other cases the condom may rupture and permit substantial transfer of bodily fluids with the consequence of possible infection or conception. Although gross rupture of a condom is relatively rare, it has been found that leaks sufficient to permit the escape of microorganisms in infectious amounts are by no means uncommon. Accordingly, the recent emergence of more serious and even fatal STDs such as AIDS has caused concern that even relatively reliable total barrier methods may not be satisfactory.

An alternative method for preventing the transmission of sexually transmitted diseases is to kill or inhibit the pathogenic microorganisms in semen and vaginal secretions so that they are incapable of infecting the tissues and causing the disease. While intravaginally placed spermatocides have been used for contraception, alone or in combination with barrier methods, antimicrobial materials have not been so used to prevent STDs, probably because many of such materials are irritating to adjacent tissues or are non-specific.

Administration of biologically active materials to the vagina for whatever purpose is usually accomplished by the use of some device that provides for convenient application of the medication by the user herself. A variety of devices exist for delivery of bioactive substances such as spermatocides and various medications. Each has its place in the medical armamentarium but each has certain deficiencies for application of contraceptive or anti-microbial agents in the context of sexual activity. Conventional vaginal suppositories and ovules may not provide medication to the entire vagina because of their shape and placement by the user in the vagina. Such suppositories are generally comprised of a material that melts at body temperature to allow the medication to spread and contact the tissues. However, when the dosage form melts, the medication may drain out of the vagina rather quickly, thus minimizing its potential effectiveness and significantly reducing the extended exposure of the tissues and pathogens to the medication which is often necessary for effective treatment. Similarly, the effective duration of contraceptives applied in this way tends to be relatively brief. In addition, such delivery vehicles, even when freshly applied, do not provide any physical barrier to deposition of male ejaculate on the cervix. Such ready access of sperm to the cervix may allow them to escape the action of spermatocides that are diffused throughout the vagina. Furthermore, because cells at the cervix are uniquely sensitive to several pathogens such as *Chlamydia trachomatis*, the absence of a barrier deprives these cells of a significant means of protection.

In order to provide for a longer retention of medication in the vagina and assure a more continuous delivery of active ingredients to the tissue, several types of vaginal rings have been proposed. Such devices are disclosed, for example, in Duncan, U.S. Pat. No. 3,545,439; Roseman, U.S. Pat. No. 3,920,805; Schopflin, U.S. Pat. Nos. 4,012,496 and 4,012,497; Wong et al., U.S. Pat. Nos. 4,237,885 and 4,286,587; and Nash et al., U.S. Patent 4,292,965. The vaginal rings are generally impregnated ith a spermatocide and are designed to be retained in the vaginal vault and to release the spermatocide slowly over a period of time to maintain an effective contraceptive concentration of the active material in the vagina. However, such devices do not prevent the direct contact of ejaculate with the tissues of the cervix, and therefore do not protect those tissues from contact with pathogenic organisms which might be contained in the ejaculate. They are also of questionable efficacy in supplying the spermatocide where it is most needed.

Another approach is to use a cervical cap or a diaphragm to serve as a mechanical barrier to the sperm and to dispense medication. These devices are designed for a relatively tight fit either to the cervix or the walls of the vagina to serve as a mechanical barrier to the passage of sperm. Such devices can be effective, especially as contraceptives and when combined with spermatocides. However, because of the need to provide a sperm-resistant seal they are frequently relatively complex devices incorporating metallic springs within a rubber or synthetic resin structure to provide the required sealing force.

Another approach to providing an effective concentration of spermatocide in the vagina is to provide a sponge impregnated with a spermatocide. Such applicators are not intended to be precisely located and may permit the contact of ejaculate with the tissues of the cervix, with the undesirable consequences outlined above.

Accordingly, a need has continued to exist for a method of contraception and prophylaxis against STDs by vaginal administration of a material that inactivates microorganisms or sperm and for a device that assures contact of such a material with microorganisms or sperm present in the male or female urogenital tract or male ejaculate.

SUMMARY OF THE INVENTION

This need has now been alleviated by the method and device of this invention, according to which one or more lectins capable of binding sperm and/or the pathogenic microorganisms responsible for STDs are administered to the vagina or site of infection prior to sexual intercourse. The lectins immobilize sperm to render them incapable of fertilization and also bind to the microorganisms to render them non-pathogenic or to the epithelial cells of the urogenital tract and vagina to prevent infection by the microorganisms.

The invention also encompasses a condom having a membrane body and a hollow interior that carries one or more lectins in its interior or impregnated into the membrane body, or coated on or linked to the membrane body.

Accordingly, it is an object of the invention to provide an improved method for prophylaxis against sexually transmitted diseases.

A further object is to provide a method of contraception.

A further object is to provide a method for binding and immobilizing pathogenic microorganisms in the vagina.

A further object is to provide a device for delivering lectins to the vagina.

A further object is to provide a composition for delivering lectins to the vagina.

A further object is to provide a condom coated with lectins.

A further object is to provide a condom having lectins covalently bound to the inner and/or outer surfaces thereof.

A further object is to provide a condom having a lumen containing lectins.

A further object is to provide a condom impregnated with lectins.

A further object is to provide a condom containing lectins within its hollow body.

A further object is to provide a condom having a reservoir of lectins on its outer surface.

Other objects of the invention will become apparent from the following detailed description.

DETAILED DESCRIPTION OF THE INVENTION AND PREFERRED EMBODIMENTS

Lectins are carbohydrate-binding proteins of nonimmune origin that agglutinate cells or precipitate polysaccharides or glycoconjugates, i.e., proteins or lipids conjugated to oligo- or polysaccharides. They are widely distributed, and have been isolated from both plant and animal sources. Their reactions with living cells are based on their ability to bind with antibody-like specificity to particular arrangements of the sugar residues that make up oligo- or polysaccharides.

The surface of eucaryotic cells contain very numerous molecules of glycoproteins and glycolipids. Similarly, the cell walls and outer membranes of bacteria and the envelopes of viruses contain structural polysaccharides and/or glycoproteins. The carbohydrate moieties of these molecules which are displayed on the cell surfaces exhibit great variety in composition and structure that serves to distinguish the types of cells and to serve as a signal to other cells or materials which come into contact with the cell. For, example, variation in the carbohydrate moieties of glycoproteins and glycolipids in the membrane of red blood cells serves as the basis for the conventional blood typing classification. When lectins recognize and bind to certain carbohydrate moieties they may serve to cross-link and agglutinate the cells bearing the binding groups, a property that earns for them the alternate name of agglutinins. Furthermore, because the same sort of carbohydrate moieties often serve as attachment points for pathogens to bind to target cells and infect or invade them, lectins may block infection of target cells by blocking the sites used by pathogens as recognition markers. The same type of specific binding occurs between sperm and egg in conception, and can be blocked by lectins. The binding ability of lectins may be very specific for certain mono- or oligosaccharides, allowing lectins to be used as a powerful tool for investigating the oligosaccharide epitopes on the surface of organisms or cells. While glycoproteins, glycolipids, and bacterial cell walls are believed to be the main lectin-binding locations on the surface of cells, it is not excluded that carbohydrate moieties derived from other molecules or cellular structures may be displayed on the cell surface or that other lectin-binding structures may be present on cell surfaces. All such lectin-binding structures may be targets for the lectins used in the method of this invention.

Current medical uses of lectins include distinguishing erythrocytes of different blood types (blood typing). More recently, lectins have been used ex-vivo in depleting T cells of patients undergoing bone marrow transplantation.

In the context of this application the term microorganism includes any microscopic organism within the categories of algae, bacteria, fungi, parasites (helminths, protozoa), viruses, and subviral agents.

Among the microorganisms that are bound by certain lectins are infectious organisms such as bacteria, protozoa, and viruses. Lectins may be used to target such microorganisms in vitro and are also capable of binding to them in vivo, thereby preventing them from infecting living cells. Human disease-causing organisms (and the diseases caused by them) that can be bound by lectins include *Neisseria gonorrhoeae* (gonorrhea); *Chlamydia trachomatis* (chlamydia, lymphogranuloma venereum); *Treponema pallidum* (syphilis); *Haemophilus ducreyi* (chancroid); *Calymmatobacterium granulomatis* (donovanosis); *Mycoplasma pneumoniae, M. hominis, M. genitalium, Ureaplasma urealyticum* (mycoplasmas); *Shigella flexneri* (shigella); *Salmonella typhi, S. choleraesuis, S. enteritidis* (salmonella); *Campylobacter fetus, C. jejuni* (campylobacter); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (many types) (genital warts); molluscum contagiosum (MSV); hepatitis A virus, hepatitis B virus, hepatitis C virus (viral hepatitis); *Trichomonas vaginalis* (trichomoniasis); yeasts such as *Candida albicans* (vulvovaginal candidiasis); *Phthirus pubis* (crab louse); and *Sarcoptes scabiei* (scabies mite). Other diseases that are transmitted by contact with bodily fluids may also be transmissible by sexual contact and are capable of being prevented by administration of lectins according to this invention. Accordingly, the term sexually transmitted diseases (STDs) is to be interpreted in this application as including any disease that is capable of being transmitted in the course of sexual contact, whether or not the genital organs are the site of the resulting pathology.

Inasmuch as lectins are also capable of agglutinating human sperm and other components of the male ejaculate, and thereby rendering the sperm immobile, intravaginal administration of lectins can also serve as a method of contraception.

According to the invention a dose of lectins adapted to bind and agglutinate pathogenic microorganisms and/or block the recognition sites on target cells is administered to the vagina prior to sexual intercourse. The active ingredients may also include lectins capable of binding and/or inactivating sperm or the male ejaculate to serve as a contraceptive.

Because of the specificity of lectins for certain microorganisms, it is preferred to administer a mixture of lectins chosen for their properties of agglutinating specific pathogens. It is also according to the invention to administer a mixture of sperm-agglutinating lectins and lectins capable of binding to pathogenic organisms to provide simultaneous contraception and protection against infection.

A representative listing of lectins, the abbreviations by which they are referred to, and their sources is given in Table 1.

TABLE 1

Lectins and Abbreviations

| Lectin | Source |
| --- | --- |
| AAnA | *Anguilla anguilla* (eel serum) |
| AAurA | *Aleuria aurantia* (orange peel fungus) |
| ABA | *Agaricus bisporus* (mushroom) |
| ABrA | *Amphicarpanea bracteata* (hog-peanut) |
| AEP | *Aedopodium podagraria* (ground elder) |
| AL | *Hippaestrum hybrid* (amaryllis bulbs) |
| APA | *Abrus precatorius* (jequirity bean) |
| AS | *Avena sativa* (oat) |
| BDA | *Bryonia dioica* (white bryony) |
| BPA | *Bauhinia purpurea alba* (camel's foot tree) |
| CA | *Cymbidium species* |
| CA | *Colchicum autumnale* (meadow saffron) |
| CAA | *Caragana arborescens* (Siberian pea tree) |
| CCA | *Cancer antennarius* (California crab) |
| ConA | *Concanavalia ensiformis* (jack bean) |
| CPA | *Cicer arietinum* (chick pea) |
| CSA | *Cytisus scoparius* (Scotch broom) |
| DBA | *Dolichos biflorus* (horse grain) |
| DSA | *Datura stramonium* (jimson weed, thorn apple) |
| ECA | *Erythrina crystagalli* (coral tree) |
| ECorA | *Erythrina coralldendron* (coral tree) |
| EEA | *Euonymus europaeus* (spindle tree) |
| EHA | *Eppactus hellebrine* |
| EHA | *Eranthis hyamalis* |
| GNA | *Galanthus nivalis* (snowdrop bulb) |
| GSA-I/GSA-II | *Griffonia simplicifolia* |
| HAA | *Helix aspersa* (garden snail) |
| HHA | *Hippeastrum hybrid* |
| HPA | *Helix pomatia* (Roman or edible snail) |
| JAC (Jacalin) | *Artocarpus integrifolia* (jackfruit) |
| LAA | *Laburnum alpinum* |

TABLE 1-continued

Lectins and Abbreviations

| Lectin | Source |
| --- | --- |
| LBA | *Phaseolus lunatis* (also limensis) (lima bean) |
| LCA (LcH) | *Lens culinaris* (lentil) |
| LEA | *Lycopersicon esculentum* (tomato) |
| LFA | *Limax flavus* (garden slug) |
| LOA | *Lathyrus oderatus* (sweet pea) |
| LDA | *Listeria ovata* |
| LTA (LOTUS) | *Lotus tetragonolobus* (asparagus pea) |
| MAA | *Maackla amurensis* (maackla) |
| MIH | *Mangifera indica* (mango) |
| MPA | *Naclura pomifera* (osage orange) |
| NPL (NPA) | *Narcissus pseudonarcissus* (daffodil) |
| ORS | *Oryza sativa* (rice) |
| PAA | *Persea americana* (avocado) |
| PHA (PHA-L) | *Phaseolis vulgaris* (red kidney bean) |
| PNA | *Arachis hypogaea* (peanut) |
| PSA | *Pisum sativum* (pea) |
| PWA | *Phytolacca americana* (pokeweed) |
| PTAgalactose | *Psophocarpus tetagonolobus* (winged bean) |
| PTAgalNac | *Psophocarpus tetagonolobus* (winged bean) |
| RCA-I/RCA-II | *Ricinus communis* (castor bean) |
| RPA | *Robinia pseudoaccacia* (black locust) |
| SBA | *Glycine max* (soybean) |
| SJA | *Sophora japonica* (Japanese pagoda tree) |
| SNA | *Sambuccus nigra* (elderberry) |
| STA | *Solanium tuberosum* (potato) |
| TKA | *Trichosanthes kinlowii* (China gourd) |
| TL | Tulipa sp. (tulip) |
| TMT | Tomentine (seaweed *Codium tomentosum*) |
| UDA | *Urtica dioica* |
| UEA-I/UEA-II | *Ulex europaeus* (gorse or furz seeds) |
| URD | *Urtica dioica* (stinging nettle) |
| VAA | *Viscum album* (European mistletoe) |
| VFA | *Vicia faba* (fava bean) |
| VGA | *Vicia graminea* |
| VRA | *Vigna radiata* (mung bean) |
| VSA | *Vicia sativa* |
| VVA | *Vicia villosa* (hairy vetch) |
| WFA | *Wisteria floribunda* (Japanese wisteria) |
| WGA | *Triticum vulgaris* (wheat germ) |
| suc-WGA(sWGA) | Succinyl WGA |

For example, *N. gonorroeae* is agglutinated by lectins that bind to N-acetyl-D-glucosamine residues on their surfaces. Such lectins include WGA and STA, which are known to agglutinate all 193 clinical isolates of *N. gonorrhoeae*. WGA is effective for such agglutination at a concentration of 3.1 micrograms per milliliter. Other lectins showing some agglutination activity with respect to *N. gonorrhoeae* include RCA-I, RCA-II, GSA-I, and SBA. Certain species of Chlamydia (*trachomatis, psittaci,* and *pneumoniae*) are known to be bound by the lectins ConA, DBA, UEA-1, SBA, and PNA. WGA also binds to the receptors on certain cells, thereby blocking infection by *C. trachomatis* and *C. psittaci*.

PHA binds to several isolates of *H. ducreyi*, suggesting that N-acetyl-D-glucosamine is present in the outer membrane polysaccharide.

WGA has been found to agglutinate a variety of bacterial cells, including *Escherichia coli, Micrococcus luteus,* and some types of *Staphylococcus aureus*. WGA, specific for N-acetyl-D-glucosamine and SBA, specific for N-acetyl-D-galactosamine, are capable of agglutinating the many bacterial species which contain these sugar residues in their cell wall polysaccharides.

Various lectins are capable of binding to certain glycoproteins present in the envelope of HIV virus. For example, ConA has been found to block infection of certain cell lines against infection by HIV in vitro, and conglutinin, a lectin derived from bovine serum, has been found to bind to the HIV envelope precursor protein gp 160, thereby preventing attachment to CD-4 receptors of target cells in vitro. GNA has been found to prevent infection of T-cells by HIV in vitro. Consequently, ConA, and GNA have been found to be effective at preventing infection of target cells by HIV-1 and HIV-2 in vitro. NPL and conglutinin have shown some activity as well.

HPA, ConA, BPA, and EHL have demonstrated efficacy in the prevention of infection of target cells by HSV-1 and HSV-2.

Lectins are also useful in aggregation of sperm. PHA, WGA, STA, ConA, PSA, APA, ECA, and ECorA have demonstrated varying degrees of efficacy in agglutination of sperm.

While the lectins discussed above and the microorganisms against which they are effective are representative of useful lectins according to the invention, it is to be understood that other lectins may be discovered which are active in the binding and agglutination of the pathogens of sexually transmitted diseases, and that the use of such lectins is intended to be included within the scope of the invention.

In determining the amount of lectin to be administered for effective binding and/or agglutination of the pathogenic microorganisms of STDs, the amount of lectin that might be bound to vaginal tissues and thereby made unavailable for agglutination of pathogens must be considered. In studies on murine vaginal tissue, DBA, LAA, LBA, LCA, LTA, RCA-I, RCA-II, SJA, STA, VGA, and WFA have been found not to bind to the tissue at any stage of the estrus cycle. In contrast, ABA, MPA, PHA-E, PHA-L, Suc-ConA, and WGA bound strongly to vaginal tissues at all stages of the estrus cycle. CSA, GSA-I, GSA-II, HAA, HPA, JAC, PNA, PAA, SBA, Suc-WGA, UEA-I, VFA, and VVA exhibited intermediate degrees of binding to murine vaginal tissues. The amount of lectin to be administered for effective prophylaxis can be determined from the relative binding effect of the various lectins to the pathogen and to the vaginal tissues.

The selection of particular lectins to be administered will depend on the diseases sought to be prevented. It is preferred to administer a mixture of lectins, each selected for best agglutinative efficacy against a particular pathogen.

The lectins may be administered in any fluid or ointment vehicle suitable for topical administration of pharmaceutical compounds. Thus creams, ointments, foams, suppositories, liposomes, ovules and the like may be formulated in which the selected lectins are dispersed in a non-toxic vehicle suitable for topical and in particular for vaginal administration. Such vehicles include oil-in-water and water-in-oil emulsions, white petrolatum, hydrophilic petrolatum, lanolin emulsions. polyethylene glycols, cocoa butter and the like. Useful vehicles include emollient oils such as water-soluble oils, e.g., liquid polyethylene glycols, which promote complete and uniform distribution of the medicament within the vagina. Representative suitable vehicles include a lubricating jelly comprised of water, propylene glycol, hydroxyethyl cellulose, benzoic acid and sodium hydroxide, a water-soluble oil comprised of water, glycerin, propylene glycol, polyquaternium #5, methyl paraben and propyl paraben; a cream comprised of benzyl alcohol, cetearyl alcohol, cetyl esters wax, octyldodecanol, polysorbate 60, purified water, and sorbitan monostearate; and a suppository comprised of polyethylene glycol (PEG) 13, PEG-32, PEG-20 stearate, benzethonium chloride, methyl paraben and lactic acid. The lectins can also be incorporated into any conventional controlled release system for releasing them gradually or in a controlled timed release profile to the site of intended activity. Such systems are well-known to those skilled in the art and include particles having coatings that dissolve or erode at different controlled rates in a body fluid, matrices, e.g., polymers from which the lectins can diffuse, erodible matrices that release lectins to the site of intended activity, or the like.

Thus, the invention encompasses a composition having one or more lectins dispersed in a pharmaceutically acceptable non-toxic vehicle. Such a composition may be in the form of a cream, lotion, ointment, salve, foam, meltable solid or the like.

According to the invention, the dispersion, suspension, emulsion, or solution of lectins in the vehicle may be applied to the site of a lesion on the external genitalia, such as the lesions produced by herpes simplex virus type 1 or type 2, chancroid, genital warts, chancre of syphilis, and the like, to prevent the transfer of pathogens. The lectins may also be introduced into the vagina in order to prevent conception or infection by pathogens introduced during sexual intercourse. The amount of lectins to be applied will be an amount that is effective to prevent conception or infection or substantially reduce the risk thereof. The amounts needed to achieve these goals will depend on the effectiveness of the individual lectins, their affinity for the target cell and the like. The effective amounts can be determined by the skilled practitioner by routine experimentation. The lectins can be delivered to the desired site of activity either as a bolus or in the form of a controlled release composition, as is well-known in the art.

Because of their ability to bind pathogenic microorganisms, thereby interfering with their mobility, attachment/adhesion, growth and reproduction, lectins are also useful in therapy of topical infections of the vagina. For those diseases wherein the pathogens grow and reproduce within the lumen of the vagina, administration of lectins, alone or in combination with other antimicrobial materials, such as antibodies, can assist in the treatment and cure of the infections Because some of the conventional means of administering medications to the vagina have certain drawbacks, as discussed above, it is preferred to incorporate the lectins into a device which will remain in the vagina and dispense the lectins over a prolonged period of time in order to maintain an effective concentration of the lectins in the vagina. Such a device may also be designed to provide a barrier that will prevent the access of pathogenic organisms into the uterus and may also function as a contraceptive device.

Thus the lectins to be introduced into the vagina can be incorporated in any conventional vaginal medication-dispensing device such as suppositories, ovules, pessaries and the like, including controlled-release systems as discussed above. The lectins may also be incorporated into conventional contraceptive devices such as diaphragms, cervical caps, vaginal sponges or the like. The lectins may be incorporated into the body of such devices or coated on the surface thereof either neat, or in a vehicle, e.g., as a dusting powder, or in a binder that provides a coating from which the lectins are released over a period of time.

A particularly preferred method of administering lectins to the urogenital tract and vagina according to the invention for contraception and prevention and therapy of STDs is to incorporate the lectins into a condom. The lectins may be coated on the inside or outside surface of the condom either neat, or in a dusting powder vehicle, or in a binder that affixes the lectins to the surface of the condom. The coating may be comprised of polymeric materials, either polymerized in situ on the surface of the condom or coated from conventional solvent or dispersant coating systems. The coating may be dry or may be a fluid having an appropriate viscosity. The lectins may be covalently bound by a linking agent to the surface of the membrane body of the condom. The binder can be of the type that releases the lectins immediately into the vagina or may provide for gradual release over a period of time. Such sustained release binders are known to those skilled in the art and may be of the same type and composition as used for solid dosage forms incorporating lectins discussed above. Lectins may be covalently bound to the surface of the membrane body of the condom by means of difunctional or polyfunctional reagents capable of reacting with the lectins and also with reactive groups present on the surface of the latex membrane body of the condom.

The lectins may also be incorporated into a structure in the condom specially adapted to hold and dispense the lectins, e.g., into one or more depressions, pockets or the like formed in the surface of the condom or a portion thereof, e.g., at the tip of the condom. The lectins contained in such a reservoir will then be released from the depressions, pockets, etc., into the vagina during sexual intercourse.

Figure 1:
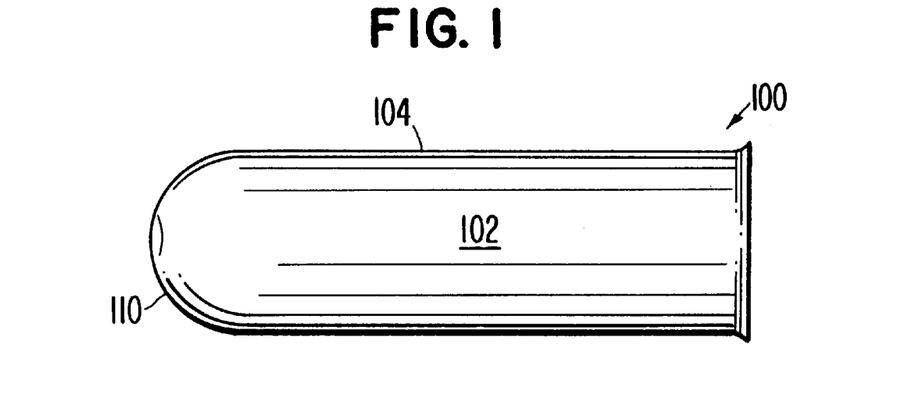
FIG. 1 is a side elevational view of a condom according to the invention.
Figure 2:
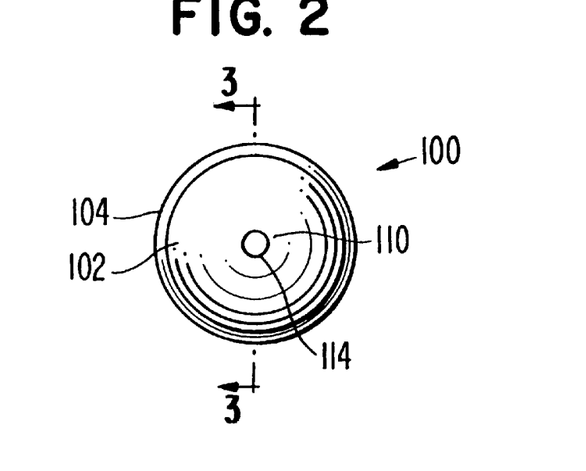
FIG. 2 is a front elevational view of a condom according to the invention.
Figure 3:
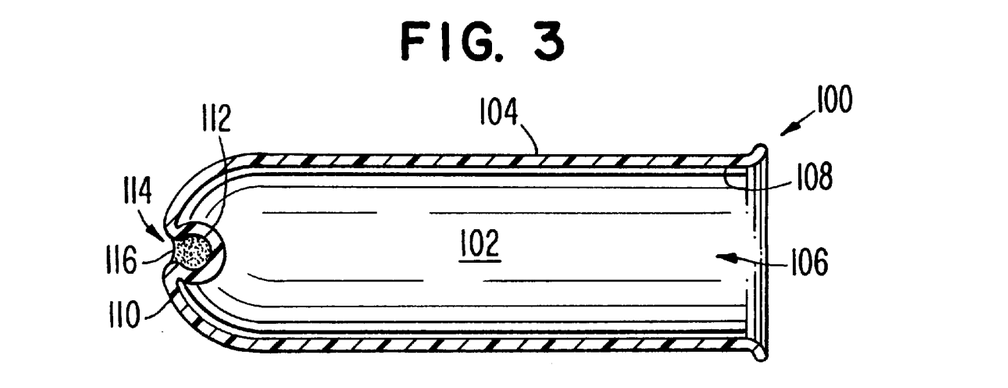
FIG. 3 is a longitudinal sectional view of the condom of the invention taken along the line 3—3 in FIG. 2.

A condom according to the invention having a reservoir containing lectins is illustrated in the drawings wherein the reference numerals refer to the same elements throughout. A condom 100 according to the invention has a membrane body 102 surrounding a hollow interior 106. The membrane body has an exterior surface 104 and an interior surface 108. At the tip 110 of the condom 100 is formed a reservoir 112 that is suitable for containing a charge of lectins, either neat or in a composition as described above, indicated as 116. The reservoir has an opening 114 through which the lectins can escape into the vagina to exercise their antimicrobial and/or contraceptive activity.

The lectins may also be incorporated into the membrane body of the condom or a portion thereof, e.g., a specially formed or thickened portion at the tip thereof. The lectins will be released from such a condom by leaching or migration from the body of the condom into the vagina during sexual intercourse. Another way in which lectins may be used in a condom for prevention of STDs or contraception is by introducing a charge of lectins inside the hollow interior of the condom. The lectins may be present in the condom neat, or in a powder vehicle, or in a fluid vehicle, preferably a thickened fluid vehicle such as a cream, salve or thickened lotion, or the like, or in a dry coating of a natural or synthetic polymer or other suitable material. When lectins are used in the interior of the condom they serve primarily as a safety factor to prevent infection or contraception in case the condom should leak or become ruptured in use. In this application, the lectins may also serve for therapy of diseases of the male urogenital tract.

The method of using lectins according to the invention to prevent the transmission of STDs can also be used in a broader application to prevent the spread of STDs accidentally during surgical or diagnostic procedures. Lectins may be incorporated into the membrane body of surgical gloves or placed within the interior of surgical gloves of the conventional type having a relatively thin rubber or polymer membrane surrounding a hollow interior and shaped to cover the hand. In this application, the lectins can protect surgeons and other medical personnel from infection by contact with blood or other bodily fluids of infected patients if the surgical gloves should leak or become punctured or cut, allowing such fluids to contact an open lesion on the hand of the wearer. The gloves will contain one or more lectins that can bind to and inactivate any pathogenic microorganisms that might find their way into the interior of the glove through a small, perhaps undetected, hole. The lectins can be placed within the glove in the form of a neat powder or a formulated powder containing the lectins in a powder vehicle, or in the form of lectins dispersed in a liquid or semisolid vehicle such as a cream, salve, lotion or the like, or in a dry coating of a natural or synthetic polymer or other suitable material.

The invention will now be illustrated by the following examples which are intended to be illustrative only and not to be interpreted as limiting the scope of the invention which is defined by the appended claims.

EXAMPLE 1

This example illustrates the utility of various lectins in binding to certain microorganisms and to seminal plasma, sperm, human serum and cervical mucus.

The efficacy of binding of various lectins to human sperm and seminal plasma and cervical mucus, an indicator of the effectiveness of such materials as vaginally-applied contraceptives, was investigated in vitro by the following procedures. Similarly the efficacy of lectin binding to *Neisseria gonorrhoeae*, the pathogen responsible for gonorrhea, was investigated by the following in vitro procedures. Such binding efficacy is an indication of the capability of such lectins to bind the pathogen and prevent infection when used intravaginally as a prophylactic material.

Growth of bacteria:

A cervical isolate of *Chlamydia trachomatis* serovar G ATCC VR-878 was grown in 175 $cm^2$ McCoy cell monolayers in the presence of 2 $\mu$g of cycloheximide per ml. The culture medium was 90% Dulbecco's Eagle's minimum essential medium-10% fetal calf serum-20 $\mu$M HEPES (pH 7.3) supplemented with 50 $\mu$g of gentamycin sulfate per ml. Elementary bodies were purified by differential centrifugation followed by density gradient centrifugation in Percoll as described by Newhall et al. (Newhall, W. J., Baheiger, B., and Jones, R. B. 1982, Analysis of the human serological response to the proteins of *Chlamydia trachomatis*, Infection Immunity 38: 1181–1189). The purified elementary bodies were washed twice in 10 mM HEPES-145 mM NaCl (pH 7.4) and resuspended in bicarbonate buffer (100 mM NaHCO3 containing 0.01% NaN3, pH 9.5). The density of elementary bodies was adjusted to a McFarland No. 2 standard using the same buffer. *Neisseria gonorrhoeae* ATCC 19424 were grown on chocolate agar plates for 48–72 hrs at 37° C. in a $CO_2$ incubator (5% $CO_2$ and 80% humidity) and were harvested by scraping bacteria from the agar surface and resuspending the cells in sterile phosphate buffered saline. The cells were washed three times by centrifugation at 5000×g and resuspended in bicarbonate buffer, the density of which was adjusted to a McFarland No. 2 standard (optical density as measured by a spectrometer—0.4 at 650 nm). The cells were stored on ice prior to immediately testing in the lectin binding assay. *Lactobacillus jensenii* ATCC 25258 was grown 48–72 hrs. at 37° C. in a shaking incubator in MRS broth at pH 5.5 containing 2% glucose. After incubation, cells were centrifuged at 5000×g for 10 min and washed twice in phosphate buffered saline, and the density was adjusted to a McFarland No. 2 standard with bicarbonate buffer. *Haemophilus ducreyi* was grown on chocolate agar plates for 72 hrs in a $CO_2$ incubator (10% $CO_2$ and 80% humidity) at 31° C. Bacteria were harvested by scraping bacteria from the agar surface and resuspending the cells in sterile phosphate buffered saline. The cells were washed three times by centrifugation at 5000×g, resuspended in bicarbonate buffer and the cell density adjusted to a McFarland No. 2 standard. The cells were stored on ice prior to immediately testing in the lectin binding assay.

Lectin Binding Assay: Biotinylated lectins were reconstituted in phosphate buffered saline (10 mM sodium phosphate-150 mM NaCl, pH 7.2) and stored in a freezer at −70° C. until used. Microtiter plates washed with 95% ethanol and dried were coated with bacteria (*Chlamydia trachomatis* or *Neisseria gonorrhoeae* or *Haemophilus ducreyi* or *Lactobacillus jensenii*) by adding 200 μl of a bacterial suspension (in bicarbonate buffer) to each well and incubating overnight at room temperature. Wells coated with bacteria were washed three times in either sodium acetate buffered saline, pH 4.0, containing 0.1% Tween detergent (ABST) or phosphate buffered saline, pH 7.2, containing 0.1% Tween (PBST). Lectins defrosted at room temperature were diluted in each buffer, and 100 μl of various lectins was added to bacteria-coated wells at a final concentration of 50 μg/ml. After incubation in a humid chamber at room temperature for 2 hours, wells were washed three times with either ABST or PBST followed by the addition to each well of 100 μl of alkaline phosphatase streptavidin (10 μg/ml). After incubation for 1 hour at room temperature, wells were washed three times with ABST or PBST and 100 μl of freshly prepared p-nitrophenylphosphate (1 mg/ml) in 0.1 M Tris buffer-0.15 M NaCl was added and color development was quantified with a spectrophotometer at 405 nm.

Cervical Mucus: A sample of cervical mucus was obtained from a healthy donor and the gel phase separated by centrifugation. The pellet was washed three times by centrifugation and the mucin stabilized and alkylated before dialysis against a low ionic strength, pH 8.0 buffer. The cervical mucus was bound to flat-bottomed plates by incubating in bicarbonate coating buffer at 4° C. overnight. The plates were washed to remove unbound ligand. Biotinylated lectins were serially diluted across the plates in the wash buffer and the plates incubated at room temperature for 2 hrs. Unbound lectin was removed by washing, and the bound lectins were tagged by incubating with streptavidin-alkaline phosphatase at room temperature for 1 hr. Unbound streptavidin-alkaline phosphatase was removed by washing and the assay completed by adding freshly prepared p-nitrophenylphosphate (1 mg/ml) in 0.1 M Tris buffer-0.15 M NaCl and monitoring the rate of color production.

Seminal Plasma and Sperm: A sample of ejaculate was donated by a healthy donor and the seminal plasma (supernatant) removed by centrifugation and frozen at −20° C. The binding assay was performed in the same way as for cervical mucus.

The sperm pellet resulting from centrifugation of the ejaculate was washed twice and total sperm count determined using a hemocytometer. Sperm were added to plates, left to settle at room temperature for 2 hrs. and fixed using glutaraldehyde. The plates were then washed and unbound sites blocked with protein solution and stored at +4° C. until use. The remainder of the binding assay was performed in the same way as for cervical mucus and seminal plasma.

Serum: A sample of blood was collected from a healthy donor, the serum separated by centrifugation and stored at −20° C. The binding assay was performed in the same way as for cervical mucus and seminal fluid.

Analysis of data: Sigma Plot was used for graphing and curve fitting of binding plots. Velocity of the color-forming reaction versus concentration of lectin added was plotted. Binding curves were fitted to the hyperbolic equation $f(x) = ax/(b+x)$ where "x" is the concentration of lectin, "f(x)" is the rate of reaction measured by change in optical density (OD) of the reaction solution per unit time, "a" is the asymptotic value of maximum reaction velocity measured as change in optical density per minute (represented in the following tables as $m_{OD}$/min) and "b" is the concentration of lectin where half of maximum binding occurs (represented in the following tables as [Lectin]$_{1/2}$ max) The binding "quotient" is defined as a/b.

The data for lectin binding to sperm, seminal plasma, cervical mucus, human serum, *Neisseria gonorrhoeae*, and *Lactobacillus jensenii* are summarized in the following tables wherein WB signifies weak binding, NB signifies no binding and N/A signifies not available.

TABLE 2

SUMMARY OF BINDING DATA

| | Quotient | | | |
|---|---|---|---|---|
| Lectin | Sperm | Seminal Plasma | Cervical Mucus | Human Serum |
| ABA | WB | 0.44 | WB | WB |
| AL | NB | NB | NB | NB |
| BPA | 0.60 | 0.86 | 20.76 | WB |
| CAA | 0.46 | 1.04 | 7.82 | WB |
| ConA | 2.59 | 2.68 | 1.11 | 3.29 |
| CPA | WB | WB | WB | WB |
| CSA | WB | 0.30 | 7.30 | WB |
| DBA | WB | WB | WB | WB |
| DSA | 1.09 | WB | WB | WB |
| ECA | WB | WB | WB | WB |
| EEA | NB | NB | 0.39 | NB |
| GNA | 0.36 | 0.58 | 0.24 | WB |
| GSA-I/GSA-II | WB | WB | WB | WB |
| HAA | NB | WB | WB | WB |
| Jacalin | 3.43 | 11.63 | 21.55 | 8.93 |
| LAA | NB | 0.57 | WB | WB |
| LBA | WB | WB | WB | WB |
| LcH | 7.26 | 2.58 | 8.64 | 1.60 |
| LES | WB | WB | WB | WB |
| LOTUS | NB | 0.94 | 4.13 | |
| MAA | NB | WB | WB | NB |
| MPA | 2.29 | 3.17 | 13.8 | 1.18 |
| PHA-L | WB | WB | WB | NB |
| PNA | WB | WB | 7.25 | NB |
| PSA | 3.44 | 2.70 | 14.5 | 1.12 |
| PTAgalactose | NB | WB | 1.31 | WB |
| PTAgalNacnb | NB | NB | 1.39 | WB |
| RPA | 1.28 | 0.84 | 0.45 | WB |
| SBA | NB | WB | WB | NB |
| SJA | NB | WB | WB | NB |
| STA | NB | WB | WB | NB |
| sWGA | 1.32 | 7.50 | WB | WB |
| TKA | WB | 0.87 | WB | WB |
| UEA-1 | WB | WB | 14.72 | WB |
| VPA | WB | 2.78 | 5.21 | 2.02 |
| VRA | WB | 3.35 | WB | WB |
| VVA | N/A | 0.81 | WB | WB |
| WFA | 2.48 | 1.96 | 26.24 | WB |
| WGA | 19.38 | 4.87 | 12.77 | 1.13 |

Notes:
1. N/A - not available
2. NB - no binding
3. WB - weak binding

TABLE 3

LECTIN BINDING TO SPERM

| Lectin | Max (m$_{OD}$/min) | [Lectin]$_{1/2\ max}$ µg/ml) | Quotient |
| --- | --- | --- | --- |
| WGA | 155 | 8 | 19.38 |
| LCH | 196 | 27 | 7.26 |
| PSA | 141 | 41 | 3.44 |
| Jacalin | 103 | 30 | 3.43 |
| ConA | 57 | 22 | 2.59 |
| WFA | 67 | 27 | 2.48 |
| MPA | 48 | 21 | 2.29 |
| sWGA | 41 | 31 | 1.32 |
| RPA | 120 | 94 | 1.28 |
| DSA | 63 | 58 | 1.09 |
| BPA | 67 | 112 | 0.60 |
| CAA | 33 | 71 | 0.46 |
| GNA | 27 | 74 | 0.36 |

TABLE 4

LECTIN BINDING TO SEMINAL PLASMA

| Lectin | Max (m$_{OD}$/min) | [Lectin]$_{1/2\ max}$ µg/ml) | Quotient |
| --- | --- | --- | --- |
| Jacalin | 93 | 8 | 11.63 |
| sWGA | 45 | 6 | 7.50 |
| WGA | 112 | 23 | 4.87 |
| VPA | 208 | 62 | 3.35 |
| MPA | 57 | 18 | 3.17 |
| VFA | 125 | 45 | 2.7 |
| PSA | 100 | 37 | 2.70 |
| ConA | 51 | 19 | 2.68 |
| LcH | 147 | 57 | 2.58 |
| WFA | 49 | 25 | 1.96 |
| CAA | 51 | 49 | 1.04 |
| LOTUS | 32 | 34 | 0.94 |
| BPA | 64 | 74 | 0.86 |
| RPA | 56 | 64 | 0.88 |
| VVA | 25 | 31 | 0.81 |
| GNA | 38 | 65 | 0.58 |
| TKA | 39 | 45 | 0.37 |
| LAA | 37 | 65 | 0.57 |
| ADA | | | 0.44 |
| CSA | 25 | 82 | 0.30 |

TABLE 5

LECTIN BINDING TO CERVICAL MUCUS

| Lectin | Max (m$_{OD}$/min) | [Lectin]$_{1/2\ max}$ µg/ml) | Quotient |
| --- | --- | --- | --- |
| WFA | 656 | 25 | 26.24 |
| Jacalin | 237 | 11 | 21.55 |
| BPA | 353 | 17 | 20.76 |
| UEA-1 | 265 | 18 | 14.72 |
| PSA | 58 | 4 | 14.50 |
| MPA | 138 | 10 | 13.80 |
| WGA | 562 | 44 | 12.77 |
| LcH | 121 | 14 | 8.64 |
| CAA | 352 | 45 | 7.82 |
| CSA | 445 | 61 | 7.30 |
| PNA | 174 | 24 | 7.25 |
| VFA | 203 | 39 | 5.21 |
| LOTUS | 194 | 47 | 4.13 |
| PTAgalNac | 110 | 79 | 1.39 |
| PTAgalactose | 113 | 86 | 1.31 |
| ConA | 41 | 37 | 1.11 |
| RPA | 25 | 56 | 0.45 |
| EEA | 27 | 70 | 0.39 |
| GNA | 13 | 55 | 0.24 |

TABLE 6

LECTIN BINDING TO HUMAN SERUM

| Lectin | Max (m$_{OD}$/min) | [Lectin]$_{1/2\ max}$ µg/ml) | Quotient |
| --- | --- | --- | --- |
| Jacalin | 134 | 15 | 8.93 |
| ConA | 79 | 24 | 3.29 |
| VFA | 107 | 53 | 2.02 |
| LcH | 123 | 7 | 1.60 |
| MPA | 40 | 34 | 1.18 |
| WGA | 160 | 142 | 1.13 |
| PSA | 84 | 75 | 1.12 |

TABLE 7

LECTIN BINDING TO *NEISSERIA GONORRHOEAE* pH4

| Lectin | Max (m$_{OD}$/min) | [Lectin]$_{1/2\ max}$ µg/ml) | Quotient |
| --- | --- | --- | --- |
| BPA | 1190 | 82 | 14.51 |
| CPA | 80 | 33 | 2.42 |
| CSA | 560 | 7 | 80.00 |
| GNA | 294 | 18 | 16.33 |
| LAA | 176 | 42 | 4.19 |
| LBA | 275 | 14 | 19.64 |
| LCH | 213 | 176 | 1.21 |
| LEA | 106 | 7 | 14.29 |
| MAA | 235 | 56 | 4.20 |
| MPA | 159 | 5 | 31.80 |
| NPA | 299 | 38 | 7.87 |
| PSA | 55 | 13 | 4.23 |
| RPA | 233 | 10 | 23.30 |
| SBA | 414 | 8 | 51.75 |
| STA | 194 | 24 | 7.57 |
| sWGA | 49 | 0.50 | 90.00 |
| TKA | 178 | 55 | 3.24 |
| VVA | 411 | 3 | 137.00 |
| WFA | 331 | 3 | 110.33 |
| WGA | 125 | 0.78 | 160.26 |

TABLE 8

LECTIN BINDING TO *LACTOBACILLUS JENSENII*

| Lectin | Max (m$_{OD}$/min) | [Lectin]$_{1/2\ max}$ µg/ml) | Quotient |
| --- | --- | --- | --- |
| ABA | 216 | 2 | 108.00 |
| BPA | 557 | 57 | 9.77 |
| GNA | 405 | 12 | 33.75 |
| Jacalin | 148 | 7 | 21.14 |
| ABA | 334 | 15 | 22.27 |
| RPA | 177 | 55 | 3.22 |
| SBA | 523 | 63 | 8.30 |
| WFA | 464 | 23 | 20.17 |
| STA | 140 | 19 | 7.37 |
| LEA | 45 | 82 | 0.55 |
| DSA | 26 | 80 | 0.33 |
| MPA | 2047 | 328 | 6.24 |
| ConA | 301 | 7 | 43.00 |
| sWGA | 96 | 64 | 1.50 |
| JAA | 136 | 17 | 8.00 |
| CSA | 624 | 387 | 1.61 |
| NPA | 425 | 36 | 11.81 |
| VVA | 260 | 33 | 7.88 |

In the above tables the affinity of the lectin for a particular substrate is inversely proportional to the maximum velocity of the color-forming reaction. Consequently, those lectins having a smaller b value ([lectin]$_{1/2}$ max) bind more firmly to the substrate. A high binding efficacy (low m$_{OD}$/min) is preferable for binding to sperm or seminal plasma for contraceptive purposes or to a pathogen, such as *Neisseria gonorrhoeae*, whose infectious activity is to be inhibited. However, it must be recognized that some microorganisms of the vaginal flora, e.g., *Lactobacillus jensenii*, are desirable and may even provide some protection against pathogenic organisms. Accordingly, if possible, it is desirable to select a lectin for contraception and/or prophylaxis against sexually transmitted diseases that combines great binding affinity for the constituents of the male ejaculate or for a pathogenic microorganism, but has a lesser, preferably minimal, binding affinity for beneficial vaginal flora. A skilled practitioner may select the most efficacious lectins by consulting the data provided in the tables of this example.

EXAMPLE 2

This example illustrates the effectiveness of lectins in inhibiting the infective activity of *Chlamydia trachomatis*.

*Chlamydia trachomatis* serovar G was cultured as described in Example 1. Lyophilized lectins were reconstituted in phosphate buffered saline (PBS) to a concentration of 1 mg/ml and frozen at −20° C. The lectins were prepared for testing in the *Chlamydia trachomatis* inactivation assay by diluting them in Minimum Essential Medium (MEM) with 10 mM HEPES and 50 µg/ml gentamycin sulfate to appropriate concentrations. *Chlamydia trachomatis* serovar G elementary bodies were added to the diluted lectins and the mixture was incubated for 1.5 hours at 37° C. After incubation, the Chlamydia-lectin mixture was added to monolayers of McCoy cells in 15×45 mm shell vials and centrifuged at 3500×g for 60 minutes at 37° C. Following centrifugation, the medium in the vials was removed and 1 ml of fresh Chlamydia overlay medium (with cycloheximide ) was added to each vial. The vials were incubated for 40–43 hours and the cells were then fixed and stained for *Chlamydia trachomatis* using Syva Microtrak™ *Chlamydia trachomatis* culture confirmation reagent.

Samples of the infected cell culture were then examined under the fluorescence microscope and evaluated for the effect of the lectin on the infectivity of the microorganism. Table 9 shows the number of mean *Chlamydia trachomatis* inclusions per 160× microscopic field on a 12 mm circular glass coverslip as a percentage of a positive control sample which was not exposed to any lectins. WGA (118%) and ConA (121%) show enhanced infectivity of *Chlamydia trachomatis* serovar G in having more inclusions per 160× field than the positive control which had not been exposed to any lectins. In contrast, exposure to Jacalin shows significantly reduced infectivity of *Chlamydia trachomatis* serovar G as evidenced by the 65% reduction in the number of inclusions per 160× field (35% of the positive control value).

TABLE 9

ANTI-CHLAMYDIAL ACTIVITY OF LECTINS

| Lectin | Concentration (µg/ml) | Infectivity (% of control) |
|---|---|---|
| ABA | 150 | 59 |
| TKA | 150 | 80 |
| WGA | 50 | 118 |
| DSA | 50 | 75 |
| WFA | 150 | 61 |
| VFA | 150 | 61 |
| ConA | 150 | 121 |

TABLE 9-continued

ANTI-CHLAMYDIAL ACTIVITY OF LECTINS

| Lectin | Concentration (µg/ml) | Infectivity (% of control) |
|---|---|---|
| Jacalin | 150 | 35 |
| MPA | 150 | 55 |

Table 10 shows the results of additional experiments for determining the anti-Chlamydia activity of selected lectins. The data in the table show that at concentrations of 150 µg/ml, the lectins designated HAA, ABA, and RPA significantly reduced infection of McCoy cells by *C. trachomatis*. However, of these three, only the lectin designated RPA was cytotoxic to McCoy cells. The lectins WGA and ConA potentiated chlamydial infectivity compared to control samples devoid of lectins.

TABLE 10

Anti-Chlamydia Activity of Lectins

| Lectin | Concentration (µg/ml) | Infectivity (a) | | | |
|---|---|---|---|---|---|
| | | Exp. 1 | Exp. 2 | Exp. 3 | Exp. 4 |
| HAA | 150 | 40.4 | 44.0 | 42.0 | 42.1 |
| ABA | 150 | 48.8 | 62.0 | 62.3 | 57.7 |
| RPA | 150 | 59.6 | 60.0 | 60.0 | 59.9 |
| WFA | 150 | 73.8 | 72.9 | 95.9 | 80.9 |
| NPA | 150 | 81.4 | 99.0 | 69.3 | 83.2 |
| GNA | 150 | 82.0 | 94.2 | 83.4 | 86.5 |
| sWGA | 100 | 95.8 | 75.8 | 93.6 | 88.4 |
| LAA | 150 | 86.7 | 92.3 | 86.5 | 88.5 |
| LBA | 150 | 88.2 | 110.0 | 74.5 | 90.9 |
| MAA | 150 | 94.4 | 101.0 | 82.5 | 92.6 |
| BPA | 150 | 93.5 | 109.0 | 101.0 | 101.0 |
| CSA | 150 | 94.9 | 124.0 | 118.0 | 112.0 |
| LEA | 150 | 110.0 | 140.0 | 102.0 | 117.0 |
| DSA | 50 | 124.0 | 135.0 | 96.1 | 118.0 |
| WGA | 50 | 109.0 | 154.0 | 144.0 | 136.0 |
| ConA | 150 | 123.0 | 168.0 | 164.0 | 149.0 |

EXAMPLE 3

This example illustrates the effectiveness of lectins in blocking the infectivity of human immunodeficiency viruses Type 1 and 2 (HIV-1/HIV-2).

A number of lectins were evaluated for possible inhibitory effects against HIV-1 and HIV-2 replication in primary infected human T-lymphocyte CEM cells. The effect of lectins on the infectivity of HIV-1 and HIV-2 toward human lymphocytes was investigated in vitro by a standard technique (Balzarini et al., 1991, *Antimicrobial Agents and Chemotherapy*, March 1991, pages 410–416) wherein the toxicity of the lectins toward the infected cells was determined (human T-lymphocytes CEM/0) and also the ability of the lectins to block the fusion of infected cells (HUT-78/HIV-1 (III$_B$) ) with other cells (MOLT/4 clone 8). The results of these tests are set forth in Tables 11 and 12 below. The results are expressed in terms of the concentration of lectins required to reduce by 50% the number of viable cells in the virus-infected cell cultures (EC$_{50}$) and in the control cell cultures (mock-infected) (CC$_{50}$) . That is, CC$_{50}$ is the cytotoxic concentration without virus and corresponds to lectin concentrations required to reduce by 50% the number of viable cells in the virus-infected cultures.

TABLE 11

Anti-Virus Activity of Lectins

| Lectin | EC$_{50}$ ($\mu$g/ml) [a] HIV-1 | HIV-2 | CC$_{50}$[b] ($\mu$g/ml) |
|---|---|---|---|
| GNA | 0.80 ± 0.1 | 1.35 ± 0.6 | >100 |
| NPA | 0.8 ± 0.2 | 0.9 ± 0.2 | >200 |
| ConA | 111.5 ± 0.79 | 1.4 ± 0.77 | 20 ± 0.71 |
| EEA | >0.16 | >0.16 | 0.5 ± 0.4 |
| MPA | >0.8 | >0.8 | 8.9 ± 3.0 |
| LCH | 11 ± 8.2 | >100 | 15 ± 2.9 |
| HAA | 15 ± 7.8 | 11.5 | 14 ± 5.9 |
| WGA | ≧16 ± 6.0 | ≧15 ± 7.8 | 13 ± 2.5 |
| PSA | 16 ± 6.0 | 82 ± 32 | 21 ± 5.7 |
| DSA | >20 | >20 | 1.5 |
| JAC | >20 | >20 | 22 ± 7.4 |
| PHA-L | 23 ± 19 | >100 | 17 ± 8.5 |
| PNA | >20 | >20 | 88 ± 11 |
| VFA | 34 ± 25 | ≧100 | 97 ± 22 |
| ABA | >100 | >100 | 73 ± 15 |
| CAA | >100 | >100 | ≧140 |
| CPA | >100 | >100 | >200 |
| CSA | >100 | >100 | >200 |
| ECA | ≧100 | ≧100 | 14 ± 2.5 |
| GSA-I | >100 | >100 | >200 |
| GSA-II | >100 | >100 | ±90 |
| LAA | >100 | >100 | >200 |
| LBA | >100 | >100 | >200 |
| LEA | >100 | >100 | >200 |
| Lotus | >100 | >100 | ≧90 |
| PAA | >100 | ≧58 | >200 |
| PTA-gal | >100 | >100 | >200 |
| PTA-galNAc | >100 | >100 | >200 |
| SJA | >100 | >100 | >200 |
| sWGA | >100 | >100 | >200 |
| SBA | 100 | >100 | ND[c] |
| TKA | >100 | >100 | 98 |
| UEA-I | >100 | >100 | >200 |
| VVA | >100 | >100 | >200 |
| WEA | >100 | >100 | >200 |

[a]: Concentration required to inhibit HIV-1 and HIV-2 induced cytopathogenicity in human T-lymphocyte CEM cells. Data are the means ± s.d. of at least three independent experiments.
[b]: Concentration required to inhibit CEM cell viability by 50%.
[c]: ND means not determined The above data indicate that only a few lectins proved inhibitory to HIV-1 and HIV-2 replication in primary infected CEM cultures under the conditions of this experiment. At concentrations ranging from 0.80 to 1.5 $\mu$g/ml, the lectins designated GNA, NPA and ConA inhibited virus-induced cytopathogenicity in CEM cells by 50%; however, the lectin designated ConA also was found to by cytotoxic to CEM cells at about 20 $\mu$g/ml.

It should also be noted that in practice in administering lectins for contraceptive, prophylactic, and/or therapeutic use, it is not always the preferred to use the lectin that binds most strongly to the target microorganism. For example, it is preferable to use lectins that will not stimulate a mitogenic response in the host.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A condom having a membrane body and a hollow interior, said condom dispensibly carrying at least one lectin capable of binding to a pathogenic microorganism or a microorganism-binding carbohydrate moiety expressed on the surface of epithelial cells lining a human male or female urogenital tract, or capable of agglutinating sperm or other components of male ejaculate.

2. The condom of claim 1 wherein said condom carries a plurality of said lectins.

3. The condom of claim 1 wherein said lectin is selected from the group consisting of AAnA, AAurA, ABA, ABrA, AL, APA, AS, BDA, BPA, CA, CAA, CCA, ConA, CPA, CSA, DBA, DSA, ECA, ECorA, EEA, GNA, GSA-I, GSA-II, HAA, HPA, Jacalin, LAA, LBA, LcH, LEA, LFA, LOA, LOTUS, MAA, MIH, MPA, NPA, PAA, PHA, PNA, PSA, PWA, PTAgalactose, PTAgalNac, RCA-I, RCA-II, RPA, SBA, SJA, SNA, STA, sWGA, TKA, TL, TMT, VAA, VFA, VGA, VRA, VSA, VVA, WFA, and WGA.

4. The condom of claim 1 wherein said lectin is contained within said hollow interior.

5. The condom of claim 4 wherein said lectin are dispersed in a biocompatible non-toxic vehicle.

6. The condom of claim 1 wherein said membrane body is impregnated with said lectin.

7. The condom of claim 1 wherein said membrane body is coated with said lectin.

8. The condom of claim 1 wherein said lectin is covalently bound to said membrane body.

9. The condom of claim 1 wherein said condom has a reservoir formed on an exterior surface of said membrane body, said reservoir containing a lectin.

10. The condom of claim 9 wherein said lectin is dispersed in a biocompatible non-toxic vehicle.

11. A surgical glove having a membrane body and a hollow interior, said glove having an interior surface and an exterior surface, said glove having at least one lectin contained within said hollow interior or coated on or linked to at least one of said interior and exterior surfaces, said lectin being capable of binding to a pathogenic microorganism.

12. The surgical glove of claim 11 wherein said surgical glove has a plurality of said lectins.

13. The surgical glove of claim 11 wherein said lectin is selected from the group consisting of AAnA, AAurA, ABA, ABrA, AL, APA, AS, BDA, BPA, CA, CAA, CCA, ConA, CPA, CSA, DBA, DSA, ECA, ECorA, EEA, GNA, GSA-I, GSA-II, HAA, HPA, Jacalin, LAA, LBA, LcH, LEA,LFA, LOA, LOTUS, MAA, MIH, MPA, NPA, PAA, PHA, PNA, PSA, PWA, PTAgalactose, PTAgalNac, RCA-I, RCA-II, RPA, SBA, SJA, SNA, STA, sWGA, TKA, TL, TMT, VAA, VFA, VGA, VRA, VSA, VVA, WFA, and WGA.

14. The surgical glove of claim 11 wherein said lectin is contained within said hollow interior.

15. The surgical glove of claim 14 wherein said lectin is dispersed in biocompatible non-toxic vehicle.

* * * * *